(12) United States Patent
Kartmann et al.

(10) Patent No.: US 9,541,622 B2
(45) Date of Patent: Jan. 10, 2017

(54) METHOD FOR DETERMINING A POSITION-DEPENDENT ATTENUATION MAP OF SURFACE COILS OF A MAGNETIC RESONANCE/PET APPARATUS

(71) Applicant: Siemens Aktiengesellschaft, Munich (DE)

(72) Inventors: René Kartmann, Nuremberg (DE); Ralf Ladebeck, Erlangen (DE); Harald H. Quick, Erlangen (DE); Stefan Rietsch, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 179 days.

(21) Appl. No.: 14/477,054

(22) Filed: Sep. 4, 2014

(65) Prior Publication Data
US 2015/0087958 A1 Mar. 26, 2015

(30) Foreign Application Priority Data
Sep. 25, 2013 (DE) .................. 10 2013 219 257

(51) Int. Cl.
*A61B 5/00* (2006.01)
*A61B 6/03* (2006.01)
(Continued)

(52) U.S. Cl.
CPC ........... *G01R 33/481* (2013.01); *A61B 5/0035* (2013.01); *A61B 5/055* (2013.01); *A61B 6/037* (2013.01);
(Continued)

(58) Field of Classification Search
CPC ....... A61B 5/0035; A61B 5/055; A61B 6/037; A61B 6/4417; A61B 6/5205; A61B 6/5247; G01R 33/3415; G01R 33/481; G01R 33/583
See application file for complete search history.

(56) References Cited

U.S. PATENT DOCUMENTS 7,923,691 B2 * 4/2011 Ladebeck .......... A61B 5/055
250/363.04
2003/0184292 A1 10/2003 Meyer et al.
(Continued)

FOREIGN PATENT DOCUMENTS

DE 10207736 A1 9/2003
DE 102010041587 A1 3/2012

OTHER PUBLICATIONS

Kartmann et al., "Simultaneous PET/MR imaging: Automatic attenuation correction of flexible RF coils", Proc. Intl. Soc. Mag. Reson. Med., 2013, vol. 21, p. 0830; 2013.
(Continued)

*Primary Examiner* — Michael Rozanski
(74) *Attorney, Agent, or Firm* — Harness, Dickey & Pierce, P.L.C.

(57) ABSTRACT

A method is disclosed for determining a position-dependent attenuation map of at least one surface coil of a combined magnetic resonance/PET apparatus. In an embodiment, the method includes acquiring magnetic resonance image data by way of the at least one surface coil during a magnetic resonance/PET examination of a patient; reconstructing the position of the at least one surface coil on the basis of the acquired magnetic resonance image data; and determining the position-dependent attenuation map of the at least one surface coil on the basis of the reconstructed position of the at least one surface coil. A magnetic resonance/PET apparatus and a computer program product, embodied to perform the method, are also disclosed.

19 Claims, 4 Drawing Sheets

(51) Int. Cl.
  *G01R 33/3415* (2006.01)
  *A61B 5/055* (2006.01)
  *G01R 33/48* (2006.01)
  *G01R 33/58* (2006.01)
  *A61B 6/00* (2006.01)

(52) U.S. Cl.
  CPC .......... *A61B 6/4417* (2013.01); *A61B 6/5205* (2013.01); *A61B 6/5247* (2013.01); *G01R 33/583* (2013.01); *G01R 33/3415* (2013.01)

(56) References Cited

U.S. PATENT DOCUMENTS

2008/0279436 A1* 11/2008 Razifar .................. G01N 23/00
                                                    382/131
2012/0074941 A1    3/2012 Grodzki

OTHER PUBLICATIONS

Paulus et al., "Simultaneous PET/MR imaging: MR-based attenuation correction of local radiofrequency surface coils", Medical Physics, vol. 39, No. 7, Jul. 2012; 2012.
German Office Action dated Aug. 13, 2015.
Kartmann et al., Simultaneous PET/MR imaging: Automatic attenuation correction of flexible RF coils", Proc. Intl Soc. Mag. Reson. Med., 2013, vol. 21, p. 0830; 2013.
Paulus et al., "Simultaneous PET/MR imaging: MR-based attenuation correction of local radiofrequency surface coils", Medical Physics, vol. 39. No. 7, Jul. 2012; 2012.

\* cited by examiner

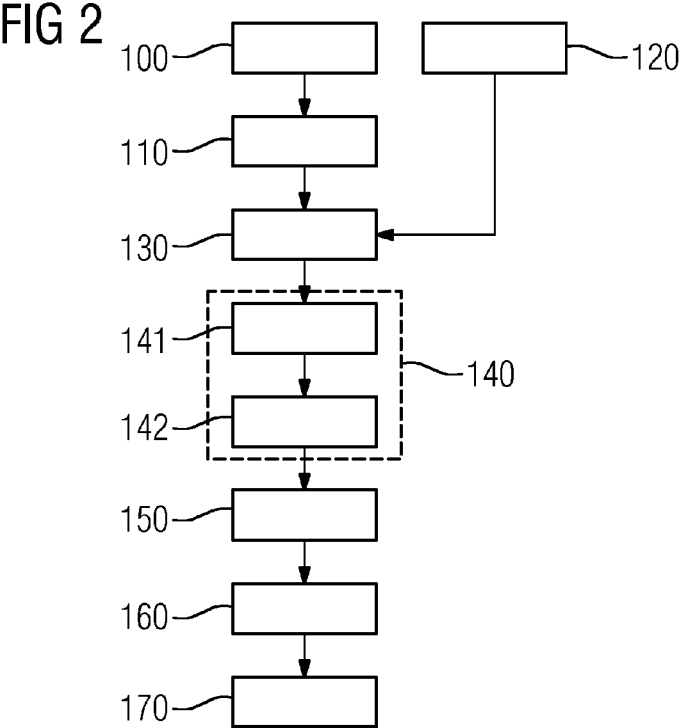
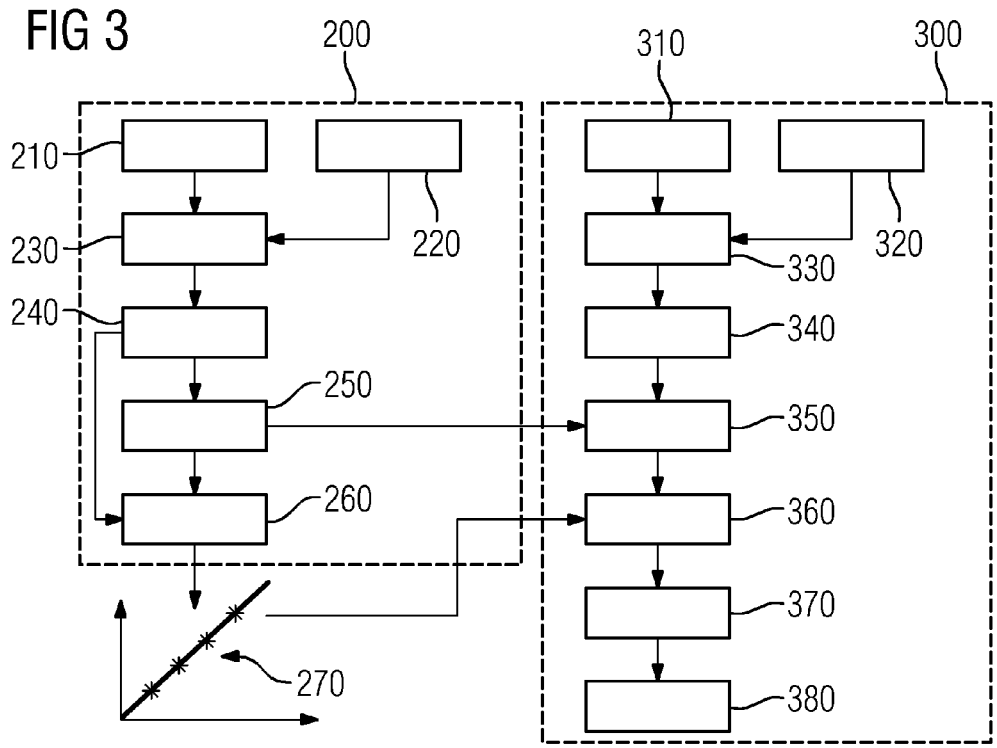

METHOD FOR DETERMINING A POSITION-DEPENDENT ATTENUATION MAP OF SURFACE COILS OF A MAGNETIC RESONANCE/PET APPARATUS

PRIORITY STATEMENT

The present application hereby claims priority under 35 U.S.C. §119 to German patent application number DE 102013219257.6 filed Sep. 25, 2013, the entire contents of which are hereby incorporated herein by reference.

FIELD

At least one embodiment of the invention generally relates to a method for determining a position-dependent attenuation map of at least one surface coil of a combined magnetic resonance/PET apparatus, to a magnetic resonance/PET apparatus and/or to a computer program product.

BACKGROUND

Local surface coils having radiofrequency antennas are used for acquiring radiofrequency signals and/or magnetic resonance signals for magnetic resonance examinations in combination with a positron emission tomography examination (PET examination). When magnetic resonance examinations are combined with PET examinations, a maximally precise knowledge of a position and/or an arrangement and/or a geometry of the surface coils is necessary in order to determine precisely a signal attenuation experienced by photons of a PET examination when passing through the surface coils. If surface coils are not taken into account in the attenuation correction, this can lead to missing PET events in the PET data and/or to image artifacts in the reconstructed image data. The difficulty that exists with regard to the attenuation correction of surface coils, however, is that the local surface coils can be arranged at different positions on the patient and are often embodied as flexible. For this reason surface coils often have an unknown geometry and/or unknown arrangement and/or unknown position during the examination.

An automatic method of detecting the position of surface coils by way of suitable additional markers is known from the publication by Kartmann et al. titled "Simultaneous PET/MR imaging: Automatic attenuation correction of flexible RF coils", Proc. Intl. Soc. Mag. Reson. Med., 2013, 21, 0830. However, additional markers also mean additional investment of effort in the coil design and/or in the retrofitting of the surface coils. Furthermore, discrete magnetic resonance markers can be virtually convoluted into the magnetic resonance image in the course of a patient examination and thus simulate non-existent lesions.

SUMMARY

At least one embodiment of the invention is directed to an improved way of detecting the position of at least one surface coil during a magnetic resonance/PET examination. Advantageous embodiments are described in the dependent claims.

A method is disclosed for determining a position-dependent attenuation map of at least one surface coil of a combined magnetic resonance/positron emission tomography apparatus (magnetic resonance/PET apparatus), comprising:

acquiring magnetic resonance image data by way of the at least one surface coil during a magnetic resonance/PET examination of a patient, reconstructing the position of the at least one surface coil on the basis of the acquired magnetic resonance image data, and determining the position-dependent attenuation map of the at least one surface coil on the basis of the reconstructed position of the at least one surface coil.

The magnetic resonance/PET apparatus according to an embodiment of the invention has a computing unit, the magnetic resonance/PET apparatus being embodied to perform a method according to an embodiment of the invention. The magnetic resonance/PET apparatus has at least one surface coil and can perform a method for determining a position-dependent attenuation map of the at least one surface coil. For this purpose the magnetic resonance/PET apparatus comprises an acquisition unit which is embodied to perform an acquisition of magnetic resonance image data by way of the at least one surface coil during a magnetic resonance/PET examination of a patient.

In addition, the magnetic resonance/PET apparatus comprises a reconstruction unit which is embodied to reconstruct the position of the at least one surface coil on the basis of the acquired magnetic resonance image data. In addition, the magnetic resonance/PET apparatus comprises a determination unit which is embodied to determine the position-dependent attenuation map of the at least one surface coil on the basis of the reconstructed position of the at least one surface coil.

Embodiment variants of the inventive magnetic resonance/PET apparatus are embodied analogously to the embodiment variants of the inventive method. Such a magnetic resonance/PET apparatus accordingly enables the automatic and efficient attenuation correction of the surface coils. Accordingly, the data generated by way of an inventive magnetic resonance/PET apparatus are not subject to the quantification errors and artifacts triggered by the presence of the surface coils.

The computing unit can be installed separately from the magnetic resonance/PET apparatus. The computing unit can be connected to the magnetic resonance/PET apparatus. By way of the computing unit the magnetic resonance/PET apparatus can advantageously perform a method according to the invention. The computing unit of the magnetic resonance/PET apparatus can perform at least parts of a method according to the invention and/or send control information to the magnetic resonance/PET apparatus and/or receive control signals from the magnetic resonance/PET apparatus which perform at least parts of a method according to the invention. For this purpose the computing unit can have control components which are necessary and/or advantageous for performing a method according to the invention. Computer programs and other software by way of which a processor of the computing unit automatically controls and/or executes a method sequence of a method according to the invention can be stored on a memory unit of the computing unit.

The computer program product according to an embodiment of the invention can be loaded directly into a memory of a programmable computing unit of a magnetic resonance/PET apparatus and has program code segments for performing a method according to an embodiment of the invention when the computer program product is executed in the computing unit of the magnetic resonance/PET apparatus.

This enables the method according to an embodiment of the invention to be performed quickly, identically repeatably and robustly.

The computer program product is configured such that it can execute the inventive method steps by way of the computing unit. For this, the computing unit must in each case fulfill the requisite conditions such as, for example, having an appropriate random access memory, an appropriate graphics card or an appropriate logic unit, so that the respective method steps can be executed efficiently. The computer program product is for example stored on a computer-readable medium or held resident on a network or server, from where it can be loaded into the processor of a local computing unit which is directly connected to the magnetic resonance/PET apparatus or can be embodied as part of the magnetic resonance/PET apparatus.

Furthermore, electronically readable control information can be stored on an electronically readable data medium. The control information can be embodied in such a way that it performs a method according to the invention when the data medium is used in a computing unit of a magnetic resonance/PET apparatus. Examples of electronically readable data media are a DVD, a magnetic tape or a USB stick on which electronically readable control information, in particular a computer program product, is stored. When the control information is read from the data medium and stored in the computing unit of the magnetic resonance/PET apparatus, all the inventive embodiment variants of the above-described methods can be performed.

BRIEF DESCRIPTION OF THE DRAWINGS

The invention is described and explained in more detail hereinbelow with reference to the example embodiments illustrated in the figures, in which:

FIG. 2 is a flowchart of a first embodiment variant of a method according to the invention, FIG. 3 is a flowchart of a second embodiment variant of a method according to the invention.

DETAILED DESCRIPTION OF THE EXAMPLE EMBODIMENTS

Figure 1:
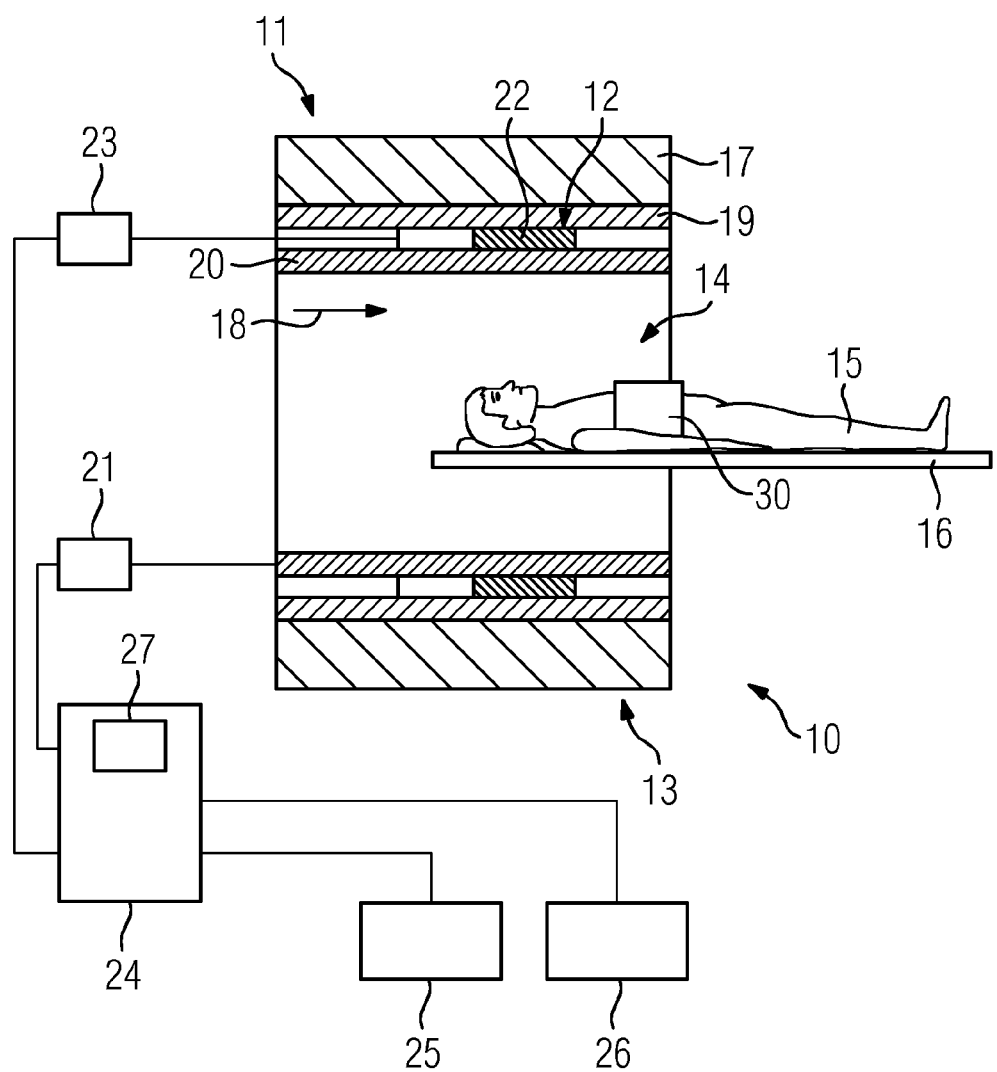
FIG. 1 shows a combined magnetic resonance/PET apparatus having a surface coil for performing a method according to an embodiment of the invention in a schematic representation.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A method is disclosed for determining a position-dependent attenuation map of at least one surface coil of a combined magnetic resonance/positron emission tomography apparatus (magnetic resonance/PET apparatus), comprising:
  acquiring magnetic resonance image data by way of the at least one surface coil during a magnetic resonance/PET examination of a patient,
  reconstructing the position of the at least one surface coil on the basis of the acquired magnetic resonance image data, and
  determining the position-dependent attenuation map of the at least one surface coil on the basis of the reconstructed position of the at least one surface coil.

The acquisition of the magnetic resonance image data by way of the at least one surface coil takes place during the magnetic resonance/PET examination. This means that the magnetic resonance image data is acquired after a patient has been positioned inside a magnetic resonance/PET apparatus in order to record diagnostic image data for diagnostic purposes. The position of the patient is preferably maintained between the acquisition of the magnetic resonance image data and the acquisition of the diagnostic image data so that there is no change in the position of the at least one surface coil between the acquisition of the magnetic resonance image data and the acquisition of the diagnostic image data. The acquisition of the magnetic resonance image data by way of the at least one surface coil can be performed in addition to the acquisition of diagnostic image data. The magnetic resonance image data can then be used to reconstruct the position of the at least one surface coil. Typically, the magnetic resonance image data is then not used for diagnostic purposes. Diagnostic image data acquired by way of the at least one surface coil can also be used for reconstructing the position of the at least one surface coil, possibly in addition to the magnetic resonance image data. The magnetic resonance image data can be acquired during a localization scan (scout view), which is typically performed at the start of the magnetic resonance/PET examination of a patient. The advantage therein is that no additional amount of time is required for the acquisition of the magnetic resonance image data during the magnetic resonance/PET examination.

By the reconstruction of the position of the at least one surface coil is meant the reconstruction of that position of the surface coil which the surface coil occupies during the magnetic resonance/PET examination with respect to the patient. The position of the surface coil can be reconstructed during and/or after the magnetic resonance/PET examination. In order to reconstruct the position of the at least one surface coil it is also possible to make reference to magnetic resonance image data acquired by way of a different coil from a surface coil, for example a whole-body coil integrated into the magnetic resonance/PET apparatus or a head-neck coil. The basic idea of reconstructing the position of the at least one surface coil on the basis of magnetic resonance image data acquired by way of the at least one surface coil is that the position of the surface coil is typically reflected in the magnetic resonance image data. Accordingly, a change in the position of the surface coil preferably leads to a change in the magnetic resonance image data. Typically, a higher magnetic resonance signal and/or signal-to-noise ratio is to be expected in the vicinity of a radiofrequency antenna unit of a surface coil. The reason for this is that the magnetic resonance signal typically decreases with increasing distance from the signal source. The position of the at least one surface coil can therefore be reconstructed on the basis of the acquired magnetic resonance signals or of the magnetic resonance signal profile, which is also referred to as the B1 signal profile, of the at least one surface coil.

The position of the at least one surface coil can be reconstructed relative to a reference point of the magnetic resonance/PET apparatus. The reference point of the magnetic resonance/PET apparatus can be the isocenter of a magnetic resonance unit or PET unit of the magnetic resonance/PET apparatus. The reference point can be the origin of the coordinate system of the magnetic resonance/PET apparatus, which lies for example at the center of the examination volume. The reference point can also be any other location in the magnetic resonance/PET apparatus. The position of the surface coil can also be reconstructed relative to a reference point of an examination object positioned in the magnetic resonance/PET apparatus. The examination object can be a patient, a user or a phantom. The reconstruction of the position of the surface coil relative to a reference point of an examination object can implicitly include determining the position relative to a reference point of the magnetic resonance/PET apparatus, since the position of the examination object in the magnetic resonance/PET apparatus is typically known, for example from the magnetic resonance image data. The reconstruction of the position of the surface coil can include reconstructing the location of the surface coil in the magnetic resonance/PET apparatus. The reconstruction of the position of the surface coil can also include reconstructing the shape and/or orientation and/or geometry of the surface coil and/or of individual coil elements of the surface coil. The position of the surface coil can be reconstructed independently of a body region that is to be examined and/or of the size of a patient.

An attenuation map of a surface coil typically comprises spatially resolved information about the attenuation values of the surface coil with respect to the attenuation of photons, in particular of photons having an energy of 511 keV. The attenuation values of the surface coil are dependent inter alia on the material and the material thickness of the surface coil. The attenuation values are typically stored in the form of linear attenuation coefficients having the unit 1/cm. An attenuation map can be used for the attenuation correction of PET data. With regard to the attenuation correction, that part of the surface coil is relevant which lies between the point of origin of the gamma quanta and the PET detector.

Determining the position-dependent attenuation map of at least one surface coil can include creating and/or loading a general attenuation map. A general attenuation map of a surface coil can be an attenuation map which is not matched to the position and geometry of the surface coil. In this case the general attenuation map can be loaded from a database. The general attenuation maps of different surface coils can be stored in the database. The database can be integrated into the magnetic resonance/PET apparatus and/or be stored on a server which can be accessed by the magnetic resonance/PET apparatus. The general attenuation map can also be loaded from a data medium. The general attenuation map of the surface coil can be generated by way of a computed tomography system, a radiotherapy apparatus or a PET transmission measurement.

A position-dependent attenuation map can be determined by way of the reconstructed actual position and/or geometry of the surface coil in the examination volume during the magnetic resonance/PET examination. For an attenuation correction of the surface coil, the position of the surface coil should be determined with an accuracy of max. 10 mm, advantageously max. 5 mm, ideally max. 3 mm. Determining the position-dependent attenuation map can include an adaptation and/or a registration and/or a transformation of the general attenuation map of the surface coil on the basis of the reconstructed position of the surface coil. The transformation of the general attenuation map can be rigid and hence comprise only a shifting of the general attenuation map in at least one spatial direction. On the other hand, the transformation can also be non-rigid and in this case change the shape of the surface coil in the general attenuation map.

By way of a method according to an embodiment of the invention the individual position of the flexible surface coil or of a plurality of flexible surface coils can be determined inherently without the use of markers or markings. Furthermore, the position is advantageously determined automatically or with only minimal user intervention. An automated attenuation correction of the surface coils in combined magnetic resonance/PET imaging is therefore possible. Additional investment of time for the acquisition of the magnetic resonance image data is not absolutely essential, since already available magnetic resonance image data can be used for determining the position of the surface coil. Accordingly, the PET data generated by way of a method according to an embodiment of the invention is advantageously not subject, or subject only to a reduced extent, to the quantification errors and artifacts triggered by the presence of the surface coils.

An embodiment variant provides that prior to the reconstruction of the position of the at least one surface coil, whole-body coil image data is acquired during the magnetic resonance/PET examination of the patient by way of a whole-body coil of the magnetic resonance/PET apparatus, wherein prior to the reconstruction of the position of the at least one surface coil, the magnetic resonance image data is normalized by way of the whole-body coil image data and the position of the at least one surface coil is reconstructed during the magnetic resonance/PET examination on the basis of the normalized magnetic resonance image data and/or the magnetic resonance image data. The whole-body coil is typically permanently integrated in the magnetic resonance/PET apparatus. Surface coils can typically be freely positioned on the patient and/or on the surface of an examination object, in particular on the surface of the body of a person subject to examination. The whole-body coil can enable magnetic resonance signals to be acquired from the whole of the examination object positioned in the magnetic resonance/PET apparatus. At the same time the whole-body coil is typically provided for emitting radiofrequency waves for exciting the spins in the examination object. In contrast to the acquisition of magnetic resonance signals by way of a surface coil, the acquisition of magnetic resonance signals by way of the whole-body coil typically leads to a largely homogeneous illumination of the examination object.

In contrast, magnetic resonance image data that has been acquired exclusively by way of surface coils is typically not illuminated homogeneously like the whole-body coil image data. Using the whole-body coil image data to normalize the magnetic resonance image data acquired by way of the surface coil can lead to a homogenization of a receive profile of the surface coil. The receive profile of a surface coil is typically dependent on the properties of the examination object.

By way of the normalization of the whole-body coil image data the receive profile of the surface coil can become independent of the properties of the examination object. The homogenized receive profile of the surface coil can be used for a more accurate reconstruction of the position of the surface coil. Preferably, therefore, the position of the surface coil is reconstructed on the basis of the magnetic resonance image data normalized by way of the whole-body coil image data. The non-normalized magnetic resonance image data can be called upon for reconstructing the position of the surface coil for specific purposes.

The whole-body coil image data can advantageously be acquired under substantially the same conditions, for example with the same position of the examination object and/or using the same imaging sequence and same sequence parameters, as the acquisition of the magnetic resonance image data by way of the surface coil. In addition to or instead of the acquisition of whole-body coil image data during the magnetic resonance/PET examination, coil sensitivity maps generated during an examination can also be referred to for reconstructing the position of the surface coil. The coil sensitivity maps can be generated automatically by way of a localization measurement.

An embodiment variant provides that a calibration process is carried out prior to the reconstruction of the position of the at least one surface coil, wherein the calibration process includes outputting training data, wherein the reconstruction of the position of the at least one surface coil is performed taking the training data into account. The calibration process can preferably be carried out prior to the magnetic resonance/PET examination of a patient. Phantom measurements and/or measurements of users and/or already acquired patient measurements can be used in the calibration process. A plurality of measurements, for example of a plurality of users, can also be used in combination in the calibration process in order to increase the accuracy of the training data. An average can then be taken for example over the training data obtained by way of the plurality of measurements or a different arithmetic operation, for example a maximum value calculation, can be applied to the training data obtained by way of the plurality of measurements. In the calibration process, the position of the surface coils is advantageously known or measurable. Training data can then be generated from the known positions of the surface coil in the calibration process and the image data acquired in the calibration process.

In a magnetic resonance/PET examination of a patient where the position of the surface coil is unknown, the training data can then enable a reconstruction of the coil position on the basis of the acquired magnetic resonance image data. In this case the reconstruction of the position of the at least one surface coil can comprise the following steps: performing at least one arithmetic operation, wherein the input data of the arithmetic operation includes the magnetic resonance image data acquired during the magnetic resonance/PET examination of the patient and the training data, and reconstructing the position of the at least one surface coil on the basis of the output data of the arithmetic operation and/or the training data. In this case the magnetic resonance image data is the magnetic resonance image data acquired by way of the surface coil during the magnetic resonance/PET examination of the patient. The magnetic resonance image data may have been normalized using the whole-body coil image data acquired by way of the whole-body coil. The arithmetic operation can correlate the magnetic resonance image data with the training data in such a way that the results of the arithmetic operation enable the position of the surface coil to be reconstructed. An advantageous example method for using a calibration process for the reconstruction of the position of the at least one surface coil comprises the registration of training image datasets acquired in the calibration process onto the magnetic resonance image data acquired during the magnetic resonance/PET examination. An attenuation map of the at least one surface coil can then be matched to the actual position of the surface coil with the aid of the obtained registration parameters. Depending on the extent of the training data, the position of the surface coil can be determined with a high degree of precision by way of this method.

An embodiment variant provides that the at least one surface coil has a plurality of coil elements, the acquisition of the magnetic resonance image data comprising an acquisition and/or reconstruction of the individual images of the coil elements. A surface coil can have 1-64 coil elements, though typically 4-8 coil elements. Each coil element, also called coil channel, can represent a radiofrequency antenna unit for receiving magnetic resonance signals, in particular a receive coil or receive unit. The coil elements can be combined into groups of several coil elements in each case. Each coil element of the surface coil can contribute with its individual signal receiving characteristics to the signal receiving characteristics of the overall surface coil. In a typical acquisition of magnetic resonance signals, the individual images of the individual coil elements are combined to form an overall image.

However, a mode can be activated on a magnetic resonance/PET apparatus so that the individual images acquired by way of the individual coil elements are stored. The individual images can also be reconstructed from an overall image. Typically, the individual images are interconnected by way of a mode matrix to form different modes. The reconstruction of the individual images can therefore entail a reverse calculation from the modes of the mode matrix to the individual images. The individual images can be normalized by way of whole-body coil image data prior to the reconstruction of the position of the at least one surface coil. The individual images can be used to deduce the position of the coil element belonging to the respective individual image of the coil element. The position of the surface coil can then be inferred from the positions of the coil elements. The more coil elements a surface coil has, the more precisely the position of the surface coil can then be determined.

An embodiment variant provides that the reconstruction of the position of the at least one surface coil comprises determining at least one reference shape for at least one coil element on the basis of the individual images. At least one reference shape can be determined for each coil element. Typically, precisely one reference shape is determined for each coil element. At least one common reference shape can also be determined for a group of coil elements. The individual image belonging to a coil element can be used for determining the reference shape of the coil element. The reference shape can be a reference point, though it can also be a reference area or a reference volume. The reference shape can enable the position of the coil elements to be determined and/or deduced. Depending on its position in space and/or its distance from the coil element of the surface coil, the reference shape can facilitate the reconstruction of the position of the coil element. The shape and/or position of the surface coil on the examination object can then be determined by way of a plurality of reference shapes. The reference shape can for example describe the signal penetration depth of the magnetic resonance signal received by way of the coil elements into the examination object. The position of the coil elements and hence the position of the surface coil can then be inferred from the signal penetration depth. Advantageously, the reference shape can therefore represent the signal profile of the coil element and/or an abstraction of the signal profile of the coil element. The determination of the reference shape can advantageously be matched to a possible deformation of the examination object.

An embodiment variant provides that the determination of the at least one reference shape comprises a threshold value analysis of a signal intensity distribution in the individual images and/or a determination of a focal point of the signal intensity distribution in the individual images. A threshold value analysis (thresholding) of the signal intensity distribution can include a segmentation of the signal intensity distribution. A suitable threshold value can be determined automatically from the magnetic resonance image data and/or be specified manually. The threshold value analysis can then extract the signal intensity distribution, also called B1 profile, of the coil element. In this case the reference volume belonging to the coil element can then be segmented in the individual images of the coil element. Toward that end the individual images can first undergo smoothing, for example by way of a Gaussian filter. The focal point of the signal intensity distribution of a coil element can be determined in the segmented individual images or non-segmented individual images. The focal point can then represent the reference point of the coil element.

An embodiment variant provides that the determination of the position-dependent attenuation map comprises integrating a general attenuation map of the at least one surface coil into a global attenuation map of the magnetic resonance/PET apparatus used for the attenuation correction of PET image datasets, wherein the integrating of the general attenuation map entails a registration of the general attenuation map on the basis of the reference shapes of the coil elements. The attenuation correction of the PET image datasets can be carried out prior to and/or during the reconstruction of the PET image datasets. Typically, the attenuation data of the examination object and/or of further hardware components, for example the patient couch or stationary magnetic resonance coils, is stored in the global attenuation map. The position-dependent attenuation map of the surface coil can then be integrated subsequently into the global attenuation map at the right point and/or with the right geometry of the surface coil. The integration can be accomplished by way of the addition of the attenuation values of the surface coil to the attenuation values of the global attenuation map. The attenuation correction of the PET image datasets can then be carried out using the combined attenuation map containing the attenuation values of the global attenuation map and the surface coil. The attenuation correction of the PET image datasets by way of the combined attenuation map can then be carried out in such a way that the events acquired by a detector are corrected taking into account the attenuation values of the combined attenuation map that lie between the detector and the origin of the gamma quanta.

The registration of the general attenuation map can include an operation in which the general attenuation map is modified in such a way that it is matched to the position and/or geometry of the surface coil. In this case a position-dependent attenuation map of the surface coil can be generated. The registration of the general attenuation map can be performed for example on the basis of the determined reference points in the manner of a landmark registration. Advantageously, known reference shapes and/or positions of the reference shapes of the coil elements are registered onto the reference shapes determined from the magnetic resonance image data and registration parameters are determined therefrom. The registration parameters can then be used in order to register the general attenuation map of the surface coil into the global attenuation map. The method of reconstructing the position of the surface coils on the basis of the reference shapes of the individual images of the coil elements is characterized by a great robustness. In principle it can be applied in the case of any examination object and does not necessarily require a previously performed calibration process. However, the accuracy of the method of reconstructing the position of the surface coils on the basis of the reference shapes of the individual images of the coil elements can potentially be improved by way of a calibration process.

An embodiment variant provides that the calibration process comprises the following steps: acquiring a plurality of magnetic resonance training image datasets of at least one training object by way of at least one surface coil, wherein in order to acquire the individual magnetic resonance training image datasets the at least one surface coil is positioned at different positions in relation to a reference point of the magnetic resonance/PET apparatus and/or a reference point of the training object, performing a main component analysis using the magnetic resonance training image datasets as input data, and outputting the training data, which comprises results of the main component analysis. Performing a calibration process is a mandatory requirement in the method presented in the following example embodiments.

The method described in the following example embodiments can be used in addition to the method described in the preceding example embodiments for reconstructing the position of the surface coil on the basis of the individual images of the coil elements and can thus improve the accuracy of the already presented method. The method described hereinbelow can also be used separately from the already presented method.

The training object can be a user. The training object can also be a phantom. The magnetic resonance training image datasets are advantageously acquired by way of a defined magnetic resonance imaging sequence, for example a 3D Flash VIBE or Dixon VIBE sequence. In this case each training image dataset can be acquired using the same imaging parameters, for example the size of the field of view. Each training image dataset can also be acquired using an identical positioning of the training object. The position of the surface coil during the acquisition of the training image datasets is advantageously known and can be stored.

For each magnetic resonance training image dataset, an image can also be acquired by way of the whole-body coil in addition to an image acquired by way of the surface coil. The former can then be called upon, as already described, for normalizing the image of the surface coil. A main component analysis is employed for generating the training data.

A main component analysis is also known as principal component analysis, the mathematical method typically comprising a principal axis transformation or singular value decomposition. Performing a principal component analysis is a practice known to the person skilled in the art, so a more detailed description of how to perform a principal component analysis will be dispensed with here. The principal component analysis can be performed by way of the training image datasets, individual images of coil elements in the training image datasets and/or individual modes of a mode matrix of the training image datasets. The principal component analysis serves to determine principal components which describe the input dataset.

Advantageously, the principal components offer a good approximation to the input dataset. In this case the principal components can describe the change in the position of the surface coil between individual magnetic resonance training image datasets. The training data output by way of the principal component analysis can therefore describe the change in the magnetic resonance training image datasets caused by the repositioning of the surface coil between the acquisitions of the magnetic resonance training image datasets. The output training data can include the principal components identified in the principal component analysis. Advantageously, the principal components are output with the associated greatest eigenvalues as training data, since the principal components best describe the magnetic resonance training image datasets. The training data can also include the known position of the surface coil during the acquisition of the magnetic resonance training image datasets. The training data can include the magnetic resonance training image datasets.

An embodiment variant provides that the acquisition of the plurality of magnetic resonance training image datasets comprises a step-by-step repositioning of the at least one surface coil for the purpose of acquiring the magnetic resonance training image datasets in at least one spatial direction. The surface coil can be repositioned prior to the acquisition of each magnetic resonance training image dataset. The repositioning can in this case be effected in regular steps. The steps can be performed spaced at intervals of a few millimeters to several centimeters, in particular spaced at intervals of one to three centimeters. A separate repositioning of the surface coil is possible in each of the three spatial directions. The repositioning can be performed in the direction of the main magnetic field and/or horizontally perpendicular thereto and/or vertically perpendicular thereto. The surface coil can be repositioned on the surface of the body of a user or on the surface of a phantom. After each displacement of the surface coil a magnetic resonance training image dataset is then acquired and possibly a whole-body coil image dataset by way of the whole-body coil in order to normalize the magnetic resonance training image dataset.

An embodiment variant provides that between the acquisition of the magnetic resonance training image datasets and the performance of the principal component analysis the magnetic resonance training image datasets are edited and the principal component analysis is performed using the edited magnetic resonance training image datasets as input data.

The magnetic resonance training image datasets can be edited for the principal component analysis either separately from one another or in combination with one another. The editing of the magnetic resonance training image datasets can enable a reduction in the dimensions of the magnetic resonance training image datasets. In this way the size of the input data can be reduced for the principal component analysis and the computing time of the principal component analysis shortened. The editing of the magnetic resonance training image datasets can include advantageous arithmetic operations. An advantageous editing of the magnetic resonance training image datasets can entail a slice-by-slice averaging of the magnetic resonance training image datasets in relation to at least one spatial direction. Other arithmetic operations are also possible, for example a median calculation or an averaging over a plurality of slices or just one part of one slice. The slice-by-slice averaging can be performed in the direction of the main magnetic field and/or horizontally perpendicular thereto and/or vertically perpendicular thereto. The edited magnetic resonance training image datasets can then be used instead of the magnetic resonance training image datasets as input data of the principal component analysis.

An embodiment variant provides that the determination of the position-dependent attenuation map comprises integrating a general attenuation map of the at least one surface coil into a global attenuation map of the magnetic resonance/PET apparatus used for the attenuation correction of PET image datasets, wherein the integrating of the general attenuation map includes a registration of the general attenuation map on the basis of the reconstructed position of the at least one surface coil. In particular the position of the surface coil reconstructed taking the training data into account can be used for the registration of the general attenuation map. The general attenuation map can therefore be registered with a high degree of precision.

An embodiment variant provides that the reconstruction of the position of the at least one surface coil comprises using information relating to a structure and/or a geometry of the at least one surface coil and/or to properties of an examination object examined during the magnetic resonance/PET examination. The known coil geometry can create restrictions with regard to the possible position of the coil elements of the surface coil. Degrees of freedom of movement of the surface coil can also be constrained in the determination of the position. Information concerning the known coil geometry can be stored in a database. Information relating to the properties of the examination object examined during the magnetic resonance/PET examination can be obtained from the acquired magnetic resonance image data. In this case the bodily contours of an examination object, for example, can be extracted from the magnetic resonance image data. The properties of the examination object can impose restrictions with regard to the position of the surface coil. Thus, for example, the surface coil or parts of the surface coil cannot lie within the body of an examination object. The body surface can also provide a point of reference for where the surface coil is positioned.

The magnetic resonance/PET apparatus according to an embodiment of the invention has a computing unit, the magnetic resonance/PET apparatus being embodied to perform a method according to an embodiment of the invention. The magnetic resonance/PET apparatus has at least one surface coil and can perform a method for determining a position-dependent attenuation map of the at least one surface coil. For this purpose the magnetic resonance/PET apparatus comprises an acquisition unit which is embodied to perform an acquisition of magnetic resonance image data by way of the at least one surface coil during a magnetic resonance/PET examination of a patient.

In addition, the magnetic resonance/PET apparatus comprises a reconstruction unit which is embodied to reconstruct the position of the at least one surface coil on the basis of the acquired magnetic resonance image data. In addition, the magnetic resonance/PET apparatus comprises a determination unit which is embodied to determine the position-dependent attenuation map of the at least one surface coil on the basis of the reconstructed position of the at least one surface coil.

Embodiment variants of the inventive magnetic resonance/PET apparatus are embodied analogously to the embodiment variants of the inventive method. Such a magnetic resonance/PET apparatus accordingly enables the automatic and efficient attenuation correction of the surface coils. Accordingly, the data generated by way of an inventive magnetic resonance/PET apparatus are not subject to the quantification errors and artifacts triggered by the presence of the surface coils.

The computing unit can be installed separately from the magnetic resonance/PET apparatus. The computing unit can be connected to the magnetic resonance/PET apparatus. By way of the computing unit the magnetic resonance/PET apparatus can advantageously perform a method according to the invention. The computing unit of the magnetic resonance/PET apparatus can perform at least parts of a method according to the invention and/or send control information to the magnetic resonance/PET apparatus and/or receive control signals from the magnetic resonance/PET apparatus which perform at least parts of a method according to the invention. For this purpose the computing unit can have control components which are necessary and/or advantageous for performing a method according to the invention. Computer programs and other software by way of which a processor of the computing unit automatically controls and/or executes a method sequence of a method according to the invention can be stored on a memory unit of the computing unit.

The computer program product according to an embodiment of the invention can be loaded directly into a memory of a programmable computing unit of a magnetic resonance/PET apparatus and has program code segments for performing a method according to an embodiment of the invention when the computer program product is executed in the computing unit of the magnetic resonance/PET apparatus. This enables the method according to an embodiment of the invention to be performed quickly, identically repeatably and robustly.

The computer program product is configured such that it can execute the inventive method steps by way of the computing unit. For this, the computing unit must in each case fulfill the requisite conditions such as, for example, having an appropriate random access memory, an appropriate graphics card or an appropriate logic unit, so that the respective method steps can be executed efficiently. The computer program product is for example stored on a computer-readable medium or held resident on a network or server, from where it can be loaded into the processor of a local computing unit which is directly connected to the magnetic resonance/PET apparatus or can be embodied as part of the magnetic resonance/PET apparatus.

Furthermore, electronically readable control information can be stored on an electronically readable data medium. The control information can be embodied in such a way that it performs a method according to the invention when the data medium is used in a computing unit of a magnetic resonance/PET apparatus. Examples of electronically readable data media are a DVD, a magnetic tape or a USB stick on which electronically readable control information, in particular a computer program product, is stored. When the control information is read from the data medium and stored in the computing unit of the magnetic resonance/PET apparatus, all the inventive embodiment variants of the above-described methods can be performed.

FIG. 1 is a schematic representation of a combined magnetic resonance/PET apparatus 10 having a surface coil 30 for performing a method according to an embodiment of the invention. The magnetic resonance/PET apparatus 10 comprises a magnetic resonance device 11 and a positron emission tomography device 12 (PET device 12).

The magnetic resonance device 11 comprises a magnet unit 13 and a patient receiving zone 14, enclosed by the magnet unit 13, for accommodating an examination object 15, in particular a patient 15, the patient receiving zone 14 being cylindrically surrounded by the magnet unit 13 in a circumferential direction. The patient 15 can be introduced into the patient receiving zone 14 by way of a patient positioning device 16 of the magnetic resonance device 11. The patient positioning device 16 is movably arranged inside the patient receiving zone 14 for this purpose.

The magnet unit 13 comprises a main magnet 17 which is configured for generating a strong and in particular constant main magnetic field 18 during the operation of the magnetic resonance device 11. The magnet unit 13 additionally has a gradient coil unit 19 for generating magnetic field gradients which is used for spatial encoding during imaging. The magnet unit 13 also comprises a whole-body coil 20 which is provided for exciting a polarization that becomes established in the main magnetic field 18 generated by the main magnet 17. The whole-body coil 20 is furthermore provided for the purpose of receiving magnetic resonance signals. The whole-body coil 20 is permanently integrated inside the magnet unit.

In order to control the main magnet of the gradient coil unit 19 and in order to control the whole-body coil 20, the magnetic resonance/PET apparatus 10, in particular the magnetic resonance device 11, has a magnetic resonance control unit 21. The magnetic resonance control unit 21 centrally controls the magnetic resonance device 11, such as in order to execute a predetermined imaging gradient echo sequence, for example. For this purpose the magnetic resonance control unit 21 comprises a gradient control unit (not shown in further detail) and a radiofrequency antenna control unit (not shown in further detail). The magnetic resonance control unit 21 furthermore includes a magnetic resonance evaluation unit for evaluating magnetic resonance image data.

The magnetic resonance device 11 has a surface coil 30 which is configured for receiving magnetic resonance signals. In preparation for a magnetic resonance examination, the surface coil 30 is applied to a region of the body of the patient 15 that is to be examined by a member of the medical staff. In the present example embodiment the surface coil 30 is formed by a whole-body antenna unit. Basically, an embodiment of the surface coil 30 as a knee antenna unit and/or back antenna unit, etc. is also conceivable at any time. It also conceivable for more than one surface coil 30 to be positioned on the patient 15. Using up to ten surface coils 30 for acquiring the magnetic resonance signals is typical.

The illustrated magnetic resonance device 11 can of course include further components that magnetic resonance devices 11 ordinarily have. The general mode of operation of a magnetic resonance device 11 is furthermore well-known to the person skilled in the art, so a detailed description of the general components will be dispensed with.

The PET device 12 comprises a plurality of positron emission tomography detector modules 22 (PET detector modules 22) which are arranged in a ring shape and encircle the patient receiving zone 14 in the circumferential direction. Each of the PET detector modules 22 has a plurality of positron emission tomography detector elements (PET detector elements) (not shown in further detail) which are arranged into a PET detector array comprising a scintillation detector array having scintillation crystals, for example LSO crystals. In addition, the PET detector modules 22 each comprise a photodiode array, for example an avalanche photodiode array, or APD photodiode array, which are arranged downstream of the scintillation detector array inside the PET detector modules 22.

Photon pairs resulting from the annihilation of a positron with an electron are detected by way of the PET detector modules 22. Trajectories of the two photons include an angle of 180°. Furthermore, the two photons each have an energy of 511 keV. In this case the positron is emitted by a radiopharmaceutical, the radiopharmaceutical being administered to the patient 15 by way of an injection. When passing through matter, the photons produced in the annihilation can be attenuated, the attenuation probability being dependent on the path length through the matter and the corresponding attenuation coefficient of the matter. In an evaluation of the PET signals it is accordingly necessary to correct the signals in respect of their attenuation by components that are situated in the beam path.

Each of the PET detector modules 22 additionally includes detector electronics comprising an electric amplifier circuit and further electronic components (not shown in any further detail). In order to control the detector electronics and the PET detector modules 22, the magnetic resonance/PET apparatus 10, in particular the PET device 12, has a PET control unit 23. The PET control unit 23 centrally controls the PET device 12. The PET control unit 23 furthermore includes a PET evaluation unit for evaluating PET data. The illustrated PET device 12 can of course include further components that PET devices 12 ordinarily have. The general mode of operation of a PET device 12 is furthermore well-known to the person skilled in the art, so a detailed description of the general components will be dispensed with.

The magnetic resonance/PET apparatus 10 also has a central computing unit 24 which for example coordinates an acquisition and/or an evaluation of magnetic resonance image data and of PET image data with one another. The computing unit 24 can be a central system control unit. Control information such as imaging parameters, for example, as well as reconstructed image data can be displayed on a display unit 25, for example on at least one monitor, of the magnetic resonance/PET apparatus 10 for an operator. The magnetic resonance/PET apparatus 10 additionally has an input unit 26 by which information and/or parameters can be input by an operator during a measurement procedure. The computing unit 24 can comprise the magnetic resonance control unit 21 and/or the PET control unit 23.

The central computing unit 24 of the magnetic resonance/PET apparatus 10 furthermore has an evaluation unit 27 which performs a reconstruction of a position of the surface coil 30 on the basis of the acquired magnetic resonance image data. With the aid of information about an embodiment and/or material properties of the surface coil 30, the evaluation unit 27 calculates a general attenuation map containing attenuation values which describes the attenuation experienced by photons when penetrating the surface coil 30 during a PET data acquisition. Based on the reconstructed position of the surface coil 30, the general attenuation map of the surface coil 30 can be integrated by the evaluation unit 27 into a global attenuation map of the magnetic resonance/PET apparatus 10 that is used for an image reconstruction of the PET data of the PET measurement.

FIG. 2 shows a flowchart of a first embodiment variant of a method according to the invention. During a magnetic resonance/PET examination of a patient 15, magnetic resonance image data is acquired in a first method step 100 by way of the magnetic resonance device 11 with the aid of at least one surface coil 30. In this case the surface coil 30 comprises a plurality of coil elements 501 (see FIG. 5). The individual images of the coil elements 501 can be acquired already during the acquisition of the magnetic resonance image data. In a further method step 110, the individual images of the coil elements 501 of the surface coil 30 can also be reconstructed from the magnetic resonance image data by way of the magnetic resonance control unit 21 and/or the computing unit 24. Subsequently or prior thereto, in a further method step 120, whole-body coil image data is acquired by way of the whole-body coil 20 of the magnetic resonance/PET apparatus and of the magnetic resonance device 11. In a further method step 130, the individual images of the coil elements 501 are normalized by way of the whole-body coil image data (see FIG. 6). This can be carried out by the magnetic resonance control unit 21 and/or the computing unit 24. A reference shape is determined 140 in the normalized individual images by way of the computing unit 24, in the course of which a reference shape, in particular a reference point, is determined for each individual image. For this purpose, in a further method step 141, the signal intensity profile 502 (see FIG. 5) of the coil element 501 of the surface coil 30 is extracted by way of a threshold value analysis. In a further method step 142, a focal point is determined as the reference point of the signal intensity profile 502. In a further method step 150, the known reference points of a general attenuation map of the surface coil 30 are registered onto the determined reference points of the coil elements 501. With the aid of the registration parameters obtained from the registration, a general attenuation map of the surface coil 30 is registered in a further method step 160 to produce a global attenuation map of the magnetic resonance/PET apparatus 10. In a further method step 170, the registered position-dependent attenuation map of the surface coil 30 is added to the global attenuation map and/or integrated into the same. The registration process of the general attenuation map is performed by way of the computing unit 24 and/or by way of the evaluation unit 27 of the computing unit 24.

FIG. 3 shows a flowchart of a second embodiment variant of a method according to the invention. Firstly, a calibration process 200 is performed for the purpose of determining training data. Then, a reconstruction process 300 is performed for the purpose of reconstructing the position of the surface coil 30 and integrating the general attenuation map of the surface coil 30 taking into account training data obtained in the calibration process 200. A determination of the position of the surface coil 30 in one spatial direction is described. The method can be performed in an identical manner for the other two spatial directions.

During the calibration process 200, in a further method step 210, a plurality of magnetic resonance training image datasets are initially acquired from a user 400 (see FIG. 4) by way of at least one surface coil 30 and the magnetic resonance device 11. For the acquisition of each magnetic resonance training image dataset, the surface coil 30 is in each case positioned at a different position relative to a reference point of the magnetic resonance/PET apparatus 10 or of the user 400. The positioning entails shifting the surface coil 30 in defined steps in one spatial direction, for example the direction of the main magnetic field 18. In a further method step 230, each magnetic resonance training image dataset is normalized by way of whole-body coil image data acquired in a further method step 220 by way of a whole-body coil 20 (see FIG. 6). This is performed by the magnetic resonance control unit 21 and/or the computing unit 24. For each magnetic resonance training image dataset, the same magnetic resonance imaging sequence, for example a 3D Flash VIBE or a Dixon VIBE sequence, is used in each case with an identical field of view both for the training image dataset and for the whole-body coil image data. Thereafter, in a further method step 240, the magnetic resonance training image datasets are edited, with the intensities of the magnetic resonance training image datasets being averaged slice by slice orthogonally to the displacement direction of the surface coil 30. In this way one-dimensional signal intensity profiles are generated by way of the computing unit 24 and/or the magnetic resonance control unit 21 from the three-dimensional magnetic resonance training image datasets. The one-dimensional signal intensity profiles are evaluated in a further method step 250 by way of a principal component analysis, the principal component having the greatest eigenvalue being output. The principal component analysis is preferably performed by way of the computing unit 24. The principal component having the greatest eigenvalue can accurately characterize the displacement of the surface coil 30 in the displacement direction. Thereafter, in a further method step 260, scalar products are calculated from the principal component having the greatest eigenvalue and the one-dimensional signal intensity profiles obtained from each magnetic resonance training image dataset. The values of the scalar products are plotted in a further method step 270 over the known positions of the surface coil during the acquisition of the magnetic resonance training image datasets and a fit curve is determined. Method steps 200 to 270 are performed by way of the computing unit 24.

For the reconstruction process 300 during the magnetic resonance/PET examination of the patient 15, magnetic resonance image data is acquired in a further method step 310 by way of at least one surface coil 30 and the magnetic resonance device 11. The magnetic resonance image data is normalized in a further method step 330 by way of whole-body coil image data acquired in a further method step 320 (see FIG. 6). In a further method step 340, the normalized magnetic resonance image data is edited once again, the magnetic resonance image data being averaged slice by slice orthogonally to the displacement direction of the calibration process 200. The magnetic resonance image data is thus reduced to a one-dimensional signal intensity profile. In a further method step 350, the scalar product is now calculated from the principal component having the greatest eigenvalue obtained from the principal component analysis and the one-dimensional signal intensity profile determined during the magnetic resonance/PET examination. The value of the scalar product is converted in a further method step 360 on the basis of the parameters of the calculated fit curve to a position of the surface coil during the magnetic resonance/PET examination in the displacement direction of the calibration process 200. The method steps 300-360 are performed by way of the computing unit 24. The method steps 300-360 can be repeated for each of the three spatial directions (displacement directions).

In this case the reconstruction of the position of the surface coil 30 is advantageously carried out using the known coil geometry of the surface coil 30 and/or the properties of an examination object 15 examined during the magnetic resonance/PET examination. In a further method step 370, a registration of the previously acquired general attenuation map of the surface coil 30 to the global attenuation map of the magnetic resonance/PET apparatus 10 is performed on the basis of the reconstructed three-dimensional position of the surface coil 30. Finally, in a further method step 380, the registered position-dependent attenuation map of the surface coil 30 is added to the global attenuation map of the magnetic resonance/PET apparatus and/or integrated into the same. The registration process of the general attenuation map can be performed by way of the computing unit 24 and/or by way of the evaluation unit 27 of the computing unit 24.

The method steps 100-380 of the method according to an embodiment of the invention illustrated in FIG. 2 and FIG. 3 are performed by the computing unit 24 in combination with the magnetic resonance/PET apparatus 10. For this purpose the computing unit 24 comprises requisite software and/or computer programs which are stored in a memory unit of the computing unit 24. The software and/or computer programs comprise program segments which are configured to perform the method according to the invention when the computer program and/or the software are/is executed in the computing unit 24 by way of a processor unit of the magnetic resonance/PET apparatus 10. A crucial point is that the reconstruction of the position of the surface coil 30 is not restricted to one surface coil 30. The positions of an arbitrary number of surface coils 30 employed in the magnetic resonance/PET examination can be reconstructed. Toward that end the calibration process 200 can also be performed using a plurality of surface coils 30.

Figure 4:
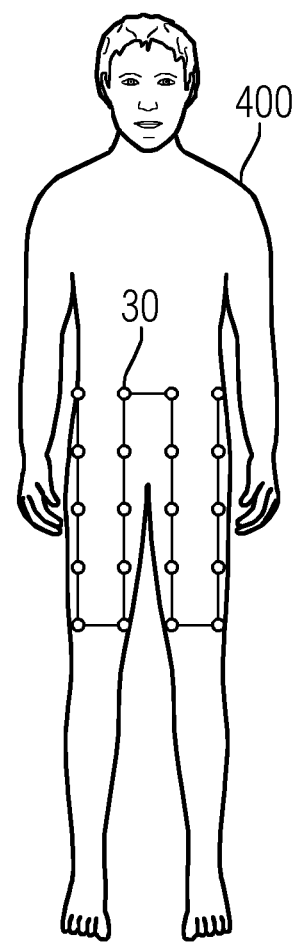
FIG. 4 shows example positions of a surface coil on a user during a calibration process of the second embodiment variant of a method according to the invention.

FIG. 4 shows example positions of a surface coil 30 on a user 400 during a calibration process 200 of the second embodiment variant of a method according to the invention. During the calibration process 200, the surface coil 30 is shifted step by step on the user 400. After each displacement of the surface coil 30, an acquisition of a magnetic resonance training image dataset and of a whole-body coil image dataset takes place by way of the magnetic resonance device 11 for the purpose of normalizing the magnetic resonance training image dataset. The displacement of the surface coil 30 over a pelvic region of the user 400 is shown. The positions of the center of the surface coil 30 are indicated by dots and the displacement of the surface coil 30 is indicated by connecting lines between the dots. In the case shown, a displacement of the surface coil 30 over twenty different positions takes place. Here, the surface coil 30 is initially positioned at five different points in the longitudinal direction of the user 400 (the z-direction) at intervals of 2 cm. The surface coil 30 is then shifted orthogonally to the longitudinal direction (x-direction) by 2 cm and a positioning of the surface coil 30 at five different points takes place once again in the z-direction. This process is repeated two more times. This can result for example in four fit curves, each having five measurement points, for the position of the surface coil 30 in the z-direction. The parameters of the fit curves can then be averaged over the four fit curves in order to make the reconstruction of the position of the surface coil 30 more accurate. Only one calibration process 200 in the pelvic region of the user 400 in two spatial directions is shown. The calibration process 200 can advantageously be performed at other points of the user 400 also, in the thoracic region for example. The calibration process 200 can also be performed for three spatial directions.

Figure 5:
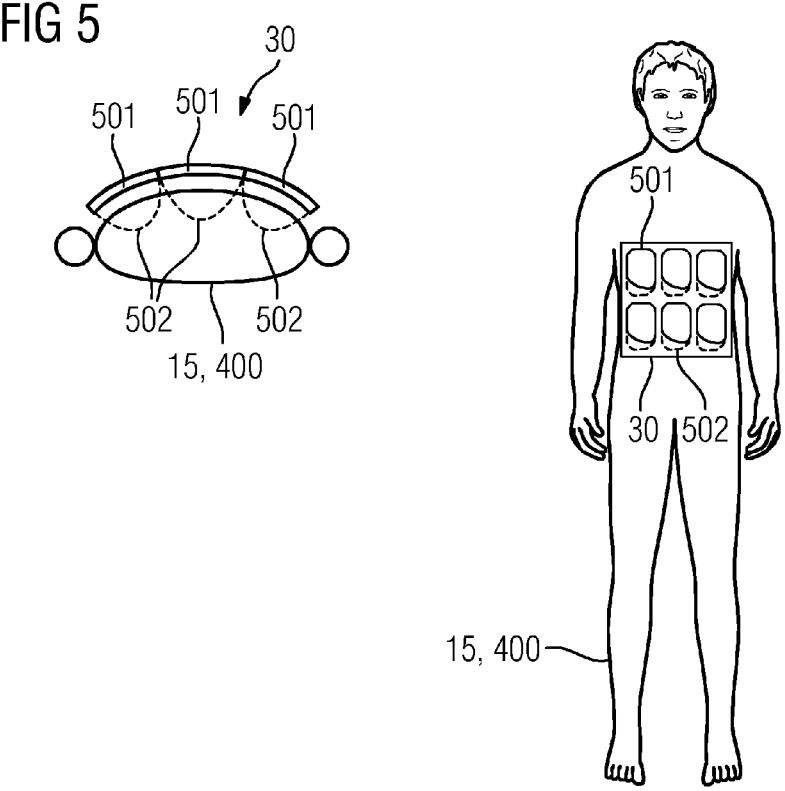
FIG. 5 shows an axial and a coronal representation of signal intensity profiles of a surface coil on an examination object.

FIG. 5 shows an axial and a coronal representation of signal intensity profiles 502 of a surface coil 30 on a user 400 or a patient 15. The surface coil 30 is constructed from a plurality of coil elements 501. In the case shown it comprises six coil elements 501 which are arranged into two groups composed of three coil elements 501 each. Each coil element 501 contributes with its individual signal intensity profile 502 to the receive profile of the overall surface coil 30. The signal intensity profiles 502 of the coil elements 501 are outlined schematically in the axial and the coronal view. They have approximately the shape of a hemisphere with a specific signal penetration depth into the examination object 15,400. In the first embodiment variant of a method according to the invention (see FIG. 2), the individual signal intensity profiles 502 of the coil elements 501 are extracted and reference shapes determined in respect of the signal intensity profiles 502. The position of the surface coil 30 is then reconstructed on the basis of the reference shapes.

Figure 6:
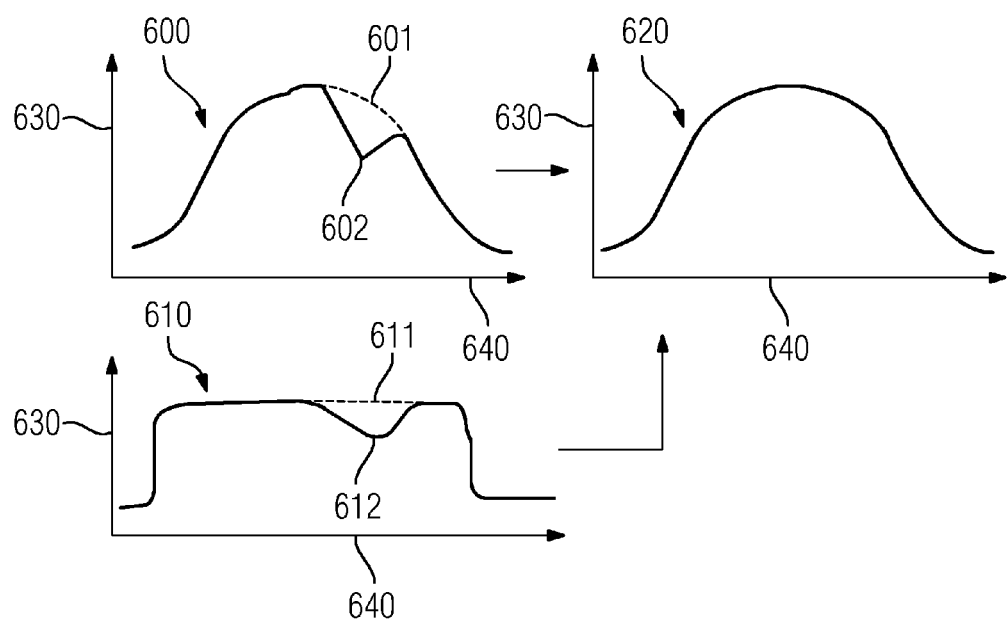
FIG. 6 shows a normalization of magnetic resonance image data using whole-body coil image data acquired by way of a whole-body coil.

FIG. 6 shows a normalization of magnetic resonance image data by way of whole-body coil image data acquired with a whole-body coil 20. The normalization is performed by way of the computing unit 24 or the magnetic resonance control unit 21. A measured signal intensity is in each case plotted on an intensity axis 630 over the space coordinate of a space axis 640. For greater clarity of illustration reasons, only a one-dimensional section, a signal profile, through the respective image data is shown. The surface coil signal profile 600 acquired by way of the surface coil has approximately a Gaussian-shaped signal profile 601. The whole-body coil signal profile 610 acquired by way of the whole-body coil has approximately a rectangular, homogeneous signal profile 611.

In the present case an examination object 15 has been acquired which has a reduced signal at a certain point. The reduced signal can originate for example from the lung of the examination object. The reduced signal expresses itself in a first signal dip 602 in the surface coil signal profile 600 and in a second signal dip 612 in the whole-body coil signal profile 610. Therefore no Gaussian-shaped signal profile 601 is present any longer in respect of the surface coil signal profile 600.

A Gaussian-shaped signal profile 601 is nevertheless desirable for a simplified and more accurate reconstruction of the position of the surface coil 30. For this reason the surface coil signal profile 600 is divided by the whole-body coil signal profile 610 during the normalization of the magnetic resonance image data. In the region of the signal dip 602,612 the lower signal in the surface coil signal profile 602 is divided by the lower signal in the whole-body coil signal profile 612. The division of the two signal profiles results approximately in the desired Gaussian-shaped surface coil signal profile 620 in the normalized magnetic resonance image data.

Although the invention has been illustrated and described in greater detail on the basis of the preferred example embodiments, the invention is nonetheless not limited by the disclosed examples and other variations can be derived herefrom by the person skilled in the art without leaving the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in greater detail by the preferred example embodiment, the invention is not restricted by the disclosed examples and other variations can be derived therefrom by the person skilled in the art, without departing from the scope of protection of the invention.

What is claimed is:

1. A method for determining a position-dependent attenuation map of at least one surface coil of a combined magnetic resonance/positron emission tomography (PET) apparatus, the at least one surface coil including a plurality of coils, the method comprising:
   acquiring magnetic resonance image data by way of the at least one surface coil during a magnetic resonance/PET examination of a patient;
   reconstructing a position of the at least one surface coil based on the acquired magnetic resonance image data;
   determining the position-dependent attenuation map of the at least one surface coil based on the reconstructed position of the at least one surface coil;
   wherein the acquiring magnetic resonance image data includes at least one of acquiring and reconstructing individual images of the plurality of coils;
   wherein the reconstructing a position of the at least one surface coil includes determining at least one reference shape for at least one of the plurality of coils based on the individual images of the plurality of coils; and
   wherein the determining at least one reference shape includes
      a threshold value analysis of a signal intensity distribution in the individual images of the plurality of coils, and
      determining a focal point of the signal intensity distribution in the individual images of the plurality of coils.

2. The method of claim 1, further comprising:
   acquiring whole-body coil image data during the magnetic resonance/PET examination of the patient by way of a whole-body coil of the combined magnetic resonance/PET apparatus;
   normalizing the magnetic resonance image data based on the whole-body coil image data; and wherein
   the position of the at least one surface coil is reconstructed based on at least one of the normalized magnetic resonance image data and the acquired magnetic resonance image data.

3. The method of claim 2, further comprising:
   performing a calibration process, the calibration process including outputting training data; and wherein
   the position of the at least one surface coil is reconstructed based on the acquired magnetic resonance image data and the training data.

4. The method of claim 3, wherein the calibration process comprises:
   acquiring a plurality of magnetic resonance training image datasets of at least one training object by way of the at least one surface coil, the at least one surface coil being positioned at different positions relative to at least one of a reference point of the combined magnetic resonance/PET apparatus and a reference point of the at least one training object;
   performing principal component analysis using the plurality of magnetic resonance training image datasets as input data; and
   outputting the training data, the training data including results of the principal component analysis.

5. The method of claim 4, wherein the acquiring a plurality of magnetic resonance training image datasets comprises:
   step-by-step repositioning of the at least one surface coil to acquire the plurality of magnetic resonance training image datasets in at least one spatial direction.

6. The method of claim 1, further comprising:
   performing a calibration process, the calibration process including outputting training data; and wherein
   the position of the at least one surface coil is reconstructed based on the acquired magnetic resonance image data and the training data.

7. The method of claim 6, wherein the calibration process further comprises:
   acquiring a plurality of magnetic resonance training image datasets of at least one training object by way of the at least one surface coil, the at least one surface coil being positioned at different positions relative to at least one of a reference point of the combined magnetic resonance/PET apparatus and a reference point of the at least one training object;
   performing principal component analysis using the plurality of magnetic resonance training image datasets as input data; and
   outputting the training data including results of the principal component analysis.

8. The method of claim 7, wherein the acquiring a plurality of magnetic resonance training image datasets comprises:
   a step-by-step repositioning of the at least one surface coil to acquire the plurality of magnetic resonance training image datasets in at least one spatial direction.

9. The method of claim 8, further comprising:
   editing the plurality of magnetic resonance training image datasets; and wherein
   the principal component analysis is performed using the edited plurality of magnetic resonance training image datasets as input data.

10. The method of claim 7, further comprising:
    editing the plurality of magnetic resonance training image datasets; and wherein
    the principal component analysis is performed using the edited plurality of magnetic resonance training image datasets as input data.

11. The method of claim 1, wherein the determining the position-dependent attenuation map comprises:
  integrating a general attenuation map of the at least one surface coil into a global attenuation map of the combined magnetic resonance/PET apparatus for attenuation correction of PET image datasets, the integrating a general attenuation map including
    registering the general attenuation map based on the at least one reference shape for the at least one of the plurality of coils.

12. The method of claim 1, wherein the determining the position-dependent attenuation map comprises:
  integrating a general attenuation map of the at least one surface coil into a global attenuation map of the combined magnetic resonance/PET apparatus for attenuation correction of PET image datasets, the integrating a general attenuation map including
    registering the general attenuation map based on the reconstructed position of the at least one surface coil.

13. The method of claim 1, wherein the reconstructing a position of the at least one surface coil is further based on (i) information relating to at least one of a structure and a geometry of the at least one surface coil, and (ii) information relating to properties of an examination object examined during the magnetic resonance/PET examination.

14. A magnetic resonance/PET apparatus comprising:
  at least one surface coil including a plurality of coils; and
  one or more processors configured to execute computer-readable instructions to determine a position-dependent attenuation map of the at least one surface coil by
    acquiring magnetic resonance image data by way of the at least one surface coil during a magnetic resonance/PET examination of a patient;
    reconstructing a position of the at least one surface coil based on the acquired magnetic resonance image data;
    determining the position-dependent attenuation map of the at least one surface coil based on the reconstructed position of the at least one surface coil;
  wherein the acquiring magnetic resonance image data includes at least one of acquiring and reconstructing individual images of the plurality of coils;
  wherein the reconstructing a position of the at least one surface coil includes determining at least one reference shape for at least one of the plurality of coils based on the individual images of the plurality of coils; and
  wherein the determining at least one reference shape includes
    a threshold value analysis of a signal intensity distribution in the individual images of the plurality of coils, and
    determining a focal point of the signal intensity distribution in the individual images of the plurality of coils.

15. A non-transitory computer-readable storage medium storing computer-readable instructions that, when executed by a programmable computing unit of a combined magnetic resonance/positron emission tomography (PET) apparatus, cause the programmable computing unit to perform a method for determining a position-dependent attenuation map of at least one surface coil of the combined magnetic resonance/PET apparatus, the at least one surface coil including a plurality of coils, and the method comprising:
  acquiring magnetic resonance image data by way of the at least one surface coil during a magnetic resonance/PET examination of a patient;
  reconstructing a position of the at least one surface coil based on the acquired magnetic resonance image data;
  determining the position-dependent attenuation map of the at least one surface coil based on the reconstructed position of the at least one surface coil;
  wherein the acquiring magnetic resonance image data includes at least one of acquiring and reconstructing individual images of the plurality of coils;
  wherein the reconstructing a position of the at least one surface coil includes determining at least one reference shape for at least one of the plurality of coils based on the individual images of the plurality of coils; and
  wherein the determining at least one reference shape includes
    a threshold value analysis of a signal intensity distribution in the individual images of the plurality of coils, and
    determining a focal point of the signal intensity distribution in the individual images of the plurality of coils.

16. A method for determining a position-dependent attenuation map of at least one surface coil of a combined magnetic resonance/positron emission tomography (PET) apparatus, the method comprising:
  acquiring magnetic resonance image data by way of the at least one surface coil during a magnetic resonance/PET examination of a patient;
  acquiring whole-body coil image data during the magnetic resonance/PET examination of the patient by way of a whole-body coil of the combined magnetic resonance/PET apparatus;
  normalizing the magnetic resonance image data based on the whole-body coil image data;
  reconstructing a position of the at least one surface coil based on at least one of the normalized magnetic resonance image data and the acquired magnetic resonance image data;
  determining the position-dependent attenuation map of the at least one surface coil based on the reconstructed position of the at least one surface coil;
  wherein the at least one surface coil includes a plurality of coils;
  wherein the reconstructing a position of the at least one surface coil includes determining at least one reference shape for at least one of the plurality of coils based on individual images of the plurality of coils; and
  wherein the determining at least one reference shape includes
    a threshold value analysis of a signal intensity distribution in the individual images of the plurality of coils, and
    determining a focal point of the signal intensity distribution in the individual images of the plurality of coils.

17. The method of claim 16, wherein the determining the position-dependent attenuation map comprises:
  integrating a general attenuation map of the at least one surface coil into a global attenuation map of the combined magnetic resonance/PET apparatus for attenuation correction of PET image datasets, the integrating a general attenuation map including
    registering the general attenuation map based on the at least one reference shape for the at least one of the plurality of coils.

18. The method of claim 16, wherein
the acquiring magnetic resonance image data includes at least one of acquiring and reconstructing the individual images of the plurality of coils.

19. A method for determining a position-dependent attenuation map of at least one surface coil of a combined magnetic resonance/positron emission tomography (PET) apparatus, the method comprising:
- acquiring magnetic resonance image data by way of the at least one surface coil during a magnetic resonance/PET examination of a patient;
- acquiring a plurality of magnetic resonance training image datasets of at least one training object by way of the at least one surface coil, the at least one surface coil being positioned at different positions relative to at least one of a reference point of the combined magnetic resonance/PET apparatus and a reference point of the at least one training object;
- performing a principal component analysis using the plurality of magnetic resonance training image datasets as input data;
- outputting training data including results of the principal component analysis;
- reconstructing a position of the at least one surface coil based on the acquired magnetic resonance image data and the training data; and
- determining the position-dependent attenuation map of the at least one surface coil based on the reconstructed position of the at least one surface coil;

wherein the at least one surface coil includes a plurality of coils;

wherein the reconstructing a position of the at least one surface coil includes determining at least one reference shape for at least one of the plurality of coils based on individual images of the plurality of coils; and wherein the determining at least one reference shape includes
- a threshold value analysis of a signal intensity distribution in the individual images of the plurality of coils, and
- determining a focal point of the signal intensity distribution in the individual images of the plurality of coils.

* * * * *